United States Patent
Herzig

Patent Number: 5,113,006
Date of Patent: May 12, 1992

[54] ORGANOSILICON COMPOUNDS CONTAINING ALKENYL GROUPS, A PROCESS FOR PREPARING THE SAME, AND THE USE OF THESE ORGANOSILICON COMPOUNDS

[75] Inventor: Christian Herzig, Taching, Fed. Rep. of Germany

[73] Assignee: Wacker-Chemie GmbH, Munich, Fed. Rep. of Germany

[21] Appl. No.: 594,791

[22] Filed: Oct. 9, 1990

[30] Foreign Application Priority Data

Oct. 27, 1989 [DE] Fed. Rep. of Germany ....... 3935775

[51] Int. Cl.$^5$ ................................................. C07F 7/08
[52] U.S. Cl. .................................... 556/453; 556/455
[58] Field of Search ................ 556/453, 455, 456, 445

[56] References Cited

U.S. PATENT DOCUMENTS

| | | | |
|---|---|---|---|
| 4,113,760 | 9/1978 | Frey et al. ........................ | 556/460 X |
| 4,874,881 | 10/1989 | Suzuki et al. ...................... | 556/453 |
| 4,876,373 | 10/1989 | Okawa et al. ...................... | 556/453 |
| 5,045,621 | 9/1991 | Suzuki .............................. | 556/453 X |

*Primary Examiner*—Arthur C. Prescott

[57] ABSTRACT

Novel organosilicon compounds containing alkenyl groups and comprising units of the average formula $$A_a R_b Si(OR^1)_c O_{\frac{4-(a+b+c)}{2}} \quad (I)$$

in which R and $R^1$ are hydrocarbon containing groups, and A is a radical of the formula $$(H_2C=CR^4CHR^3OR^2)_x H_{1-x}\overset{|}{C}=CH_{2-y}(R^2OCHR^3CR^4=CH_2)_y$$

in which $R^2$, $R^3$ and $R^4$ are hydrocarbon containing groups; x is 0 or 1; y is 0 or 1, with the proviso that the sum x+y is 1 or 2; a is 0 or 1, with an average of 0.003 to 1.0; b is 0, 1, 2 or 3, with an average of 0.0 to 3.0; c is 0, 1, 2 or 3; with an average of 0.0 to 3.0; and the sum $a+b+c \leq 4$, with an average of 1.5 to 4.0, with the proviso that each molecule contains at least one A radical and a method for preparation of the novel compounds are disclosed.

11 Claims, No Drawings

ORGANOSILICON COMPOUNDS CONTAINING ALKENYL GROUPS, A PROCESS FOR PREPARING THE SAME, AND THE USE OF THESE ORGANOSILICON COMPOUNDS

The present invention relates to organosilicon compounds and more particularly to organosilicon compounds containing alkenyl groups and to a process for preparing the same.

BACKGROUND OF THE INVENTION

U.S. Pat. No. 4,609,574 (published Sep. 2, 1986, J. R. Keryk et al, Dow Corning Corporation), disclosed that Si-bonded higher alkenyl groups, such as, for example, 5-hexenyl groups in organopolysiloxane compositions are more reactive than Si-bonded vinyl groups toward Si-hydrogen. The organopolysiloxanes containing higher alkenyl groups can be prepared by reacting an organopolysiloxane containing Si-bonded hydrogen with an α,w-diene, but multiple addition reactions always occur. The organopolysiloxanes containing higher alkenyl groups are therefore preferably obtained by reacting an α,w-diene in large excess with the silane containing Si-bonded hydrogen and subsequently this silane is hydrolyzed and equilibrated with an organopolysiloxane.

E. Lukevits et al, Zhurnal Obshchei Khimii, Vol. 56, 140-143, 1986 (Chemical Abstracts, Vol. 105, 226720 h, 1986) describe the hydrosilylation of alkenes and alkynes using dimethyl(2-thienyl)silane. The triple bond is more reactive here than the double bond.

Therefore, it is an object of the present invention to provide organosilicon compounds containing alkenyl groups which can be prepared in a simple process with high selectivity.

SUMMARY OF THE INVENTION

The foregoing objects and others which will become apparent from the following description are accomplished in accordance with this invention, generally speaking, by providing organosilicon compounds containing alkenyl groups and having units of the average formula $$A_a R_b Si(OR^1)_c O_{\frac{4-(a+b+c)}{2}} \quad (1)$$

in which the R radicals are the same or different monovalent hydrocarbon radicals having from 1 to 18 carbon atom(s) per radical and halogenated hydrocarbon radicals having from 1 to 18 carbon atom(s) per radical, the $R^1$ radicals are the same or different alkyl radicals having from 1 to 8 carbon atom(s) per radical, which may be substituted by an ether oxygen atom, and A is a radical of the formula

in which $R^2$ is an alkylene radical having from 1 to 4 carbon atom(s) per radical; $R^3$ is a hydrogen atom or a methyl radical; $R^4$ is a hydrogen atom or a methyl or ethyl radical; x is 0 or 1, y is 0 or 1, with the proviso that the sum of x+y is 1 or 2; a is 0 or 1, with an average of from 0.003 to 1.0; b is 0, 1, 2 or 3, with an average of from 0.0 to 3.0; c is 0, 1, 2 or 3, with an average of from 0.0 to 3.0; and the sum a+b+c≦4, with an average of from 1.5 to 4.0; with the proviso that each molecule contains at least one radical A.

The invention furthermore relates to a process for the preparation of the organosilicon compounds containing alkenyl groups, which comprises subjecting an organic compound of the formula

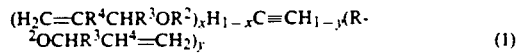

in which $R^2$, $R^3$ and $R^4$ are as defined above, to an addition reaction with an organosilicon compound (2) containing at least one Si-bonded hydrogen atom in its molecule, in the presence of a catalyst (3) which promotes the addition reaction of Si-bonded hydrogen with an aliphatic multiple bond.

DETAILED DESCRIPTION OF THE INVENTION

The organosilicon compounds of this invention are preferably silanes or organopolysiloxanes.

The organosilicon compounds of this invention preferably have an average molecular weight of from 170 to 100,000 g/mol, more preferably from 170 to 10,000 g/mol, and preferably have a viscosity of from 1 to 1,000,000 mm$^2$·s$^{-1}$ at 25° C., more preferably of from 1 to 20,000 mm$^2$·s$^{-1}$ at 25° C.

Examples of radicals represented by R are alkyl radicals, such as the methyl, ethyl, n-propyl, isopropyl, 1-n-butyl, 2-n-butyl, isobutyl, tert-butyl, n-pentyl, isopentyl, neopentyl and tert-pentyl radicals, hexyl radicals, such as the n-hexyl radical, heptyl radicals, such as the n-heptyl radical, octyl radicals, such as the n-octyl radical and isooctyl radicals, such as the 2,2,4-trimethylpentyl radical, nonyl radicals, such as the n-nonyl radical, decyl radicals, such as the n-decyl radical, dodecyl radicals, such as the n-dodecyl radical, and octadecyl radicals, such as the n-octadecyl radical; cycloalkyl radicals, such as cyclopentyl, cyclohexyl and cycloheptyl radicals, and methylcyclohexyl radicals; aryl radicals, such as the phenyl, naphthyl, anthryl and phenanthryl radicals; alkaryl radicals, such as o-, m- and p-tolyl radicals, xylyl radicals and ethylphenyl radicals; and aralkyl radicals, such as the benzyl and the α- and β-phenylethyl radicals. The methyl radical is preferred.

Examples of halogenated radicals represented by R are haloalkyl radicals, such as the 3,3,3-trifluoro-n-propyl radical, the 2,2,2,2',2',2'-hexafluoroisppropyl radical, and heptafluoroisopropyl radical, and haloaryl radicals, such as the o-, m- and p-chlorophenyl radicals.

Examples of alkyl radicals represented by $R^1$ are methyl, ethyl, n-propyl, isopropyl, 1-n-butyl, 2-n-butyl, isobutyl and tert-butyl. The methyl and ethyl radicals are preferred. Examples of alkyl radicals represented by $R^1$, which are substituted by an ether oxygen atom, are the methoxyethyl and ethoxy-ethyl radicals.

Examples of alkylene radicals represented by $R^2$ are those of the formula —CH$_2$—, —CH(CH$_3$)—, —C(CH$_3$)$_2$—, —C(CH$_3$)(C$_2$H$_5$)—, —(CH$_2$)$_2$— and —(CH$_2$)$_4$—.

The $R^3$ and $R^4$ radicals are preferably hydrogen atoms; x and y preferably each have a value of 1.

Examples of radicals represented by A are those of the formulas

—CH=CHCH$_2$OCH$_2$CH=CH$_2$ and

-continued $$H_2C=CCH_2OCH_2CH=CH_2,$$
$$|$$

$$-CH=CHCH_2OCH(CH_3)CH=CH_2 \text{ and}$$

$$H_2C=CCH_2OCH(CH_3)CH=CH_2,$$
$$|$$

$$-CH=CHCH(CH_3)OCH_2CH=CH_2 \text{ and}$$

$$H_2C=CCH(CH_3)OCH_2CH=CH_2,$$
$$|$$

$$-CH=CHCH(CH_3)OCH_2C(CH_3)=CH_2 \text{ and}$$

$$H_2C=CCH(CH_3)OCH_2C(CH_3)=CH_2.$$
$$|$$

$$H_2C=CHCH_2OCH_2C=CHCH_2OCH_2CH=CH_2.$$
$$|$$

$$H_2C=CHCH_2OCH(CH_3)C=CHCH(CH_3)OCH_2CH=CH_2 \text{ and}$$
$$|$$

$$H_2C=C(CH_3)CH_2OCH_2C=CHCH_2OCH_2C(CH_3)=CH_2.$$
$$|$$

where the radical of the formula $$H_2C=CHCH_2OCH_2C=CHCH_2OCH_2CH=CH_2$$
$$|$$

is an example of a preferred radical A.

Preferred silanes containing alkenyl groups are those of the formula $$AR_dSi(OR^1)_{3-d} \quad (II)$$

in which A, R and R¹ are the same as above, and d is 0, 1 or 2.

Preferred organopolysiloxanes containing alkenyl groups are those of the formula $$A_gR_{3-g}SiO(SiR_2O)_n(SiRAO)_mSiR_{3-g}A_g \quad (III)$$

in which A and R are the same as above; g is 0 or 1; n is 0 or an integer from 1 to 1,500; and m is 0 or an integer from 1 to 100, with the proviso that each molecule contains at least one A radical.

Examples of organic compounds (1) which are employed in the process of this invention are those of the formulas $$HC\equiv CCH_2OCH_2CH=CH_2,$$

$$HC\equiv CCH_2OCH(CH_3)CH=CH_2,$$

$$HC\equiv CCH(CH_3)OCH_2CH=CH_2,$$

$$HC\equiv CCH(CH_3)OCH_2C(CH_3)=CH_2,$$

$$H_2C=CHCH_2OCH_2C\equiv CCH_2OCH_2CH=CH_2,$$

$$H_2=CHCH_2OCH(CH_3)C\equiv CCH(CH_3)OCH_2CH=CH_2 \text{ and}$$

$$H_2C=C(CH_3)CH_2OCH_2C\equiv CC-H_2OCH_2C(CH_3)=CH_2.$$

Processes for preparing the organic compounds (1) are described in EP-B 46,731 (published Oct. 3, 1984, F. Lohse et al, Ciba Geigy AG) and U.S. Pat. No. 3,149,168 (published Sep. 15, 1964, S. I. Karlan et al, Thiokol Chemical Corp.).

The organosilicon compound (2) containing at least one Si-bonded hydrogen atom per molecule is preferably a silane containing one Si-bonded hydrogen atom per molecule or an organopolysiloxane containing one Si-bonded hydrogen atom per molecule, of the formula $$H_eR_fSiO_{\frac{4-(e+f)}{2}}, \quad (IV)$$

in which R is the same as above; e is 0 or 1, with an average of from 0.003 to 1.0; f is 0, 1, 2 or 3, with an average of from 0.0 to 3.0; and the sum of e+f does not exceed 3.

The organopolysiloxanes containing at least one Si-bonded hydrogen atom preferably contain at least 0.04 percent by weight, and more preferably from 0.1 to 1.6 percent by weight, of Si-bonded hydrogen, and their average viscosity is preferably 2 to 20,000 mm²·s⁻¹ at 25° C., and more preferably from 2 to 2,000 mm²·s⁻¹ at 25° C.

The silanes containing one Si-bonded hydrogen atom per molecule are preferably those of the formula $$HR_dSi(OR^1)_{3-d} \quad (V),$$

in which R, R¹ and d are the same as above.

The organopolysiloxanes containing at least one Si-bonded hydrogen atom per molecule are preferably those of the formula $$H_hR_{3-h}SiO(SiR_2O)_o(SiRHO)_pSiR_{3-h}H_h \quad (VI).$$

in which R is the same as above; h is 0 or 1; o is 0 or an integer from 1 to 1,500; and p is 0 or an integer from 1 to 100.

A preferred example of a silane of formula (V) is triethoxysilane. Preferred examples of organopolysiloxanes of formula (VI) are copolymers comprising dimethylhydrogensiloxane and dimethylsiloxane units, copolymers comprising dimethylhydrogensiloxane, dimethylsiloxane and methylhydrogensiloxane units, copolymers comprising trimethylsiloxane and methylhydrogensiloxane units, and copolymers comprising trimethylsiloxane, dimethylsiloxane and methylhydrogensiloxane units.

Processes for preparing the organopolysiloxanes containing at least one Si-bonded hydrogen atom per molecule, including those of the preferred type, are generally known.

In the process of this invention, the organic compound (1) is preferably used in such amounts that from about 1 to 2 mol, preferably from about 1.05 to 1.20 mol, of the organic compound (1) is present per gram-atom of Si-bonded hydrogen in the organosilicon compound (2).

In the process of this invention, the catalysts (3) which promote the addition reaction of Si-bonded hydrogen to an aliphatic multiple bond may be the same catalysts which have been or could have been employed heretofore to promote the addition reaction of Si-bonded hydrogen to an aliphatic multiple bond. The catalyst (3) is preferably a metal from the platinum metal group of a compound or a complex of a metal from the platinum metal group. Examples of catalysts of this type are metallic and finely divided platinum, which may be supported on carriers, such as silicon dioxide, aluminum oxide or activated charcoal, compounds or complexes of platinum, such as platinum halides, for example $PtCl_4$, $H_2PtCl_6\cdot 6H_2O$, $Na_2PtCl_4\cdot 4H_2O$, platinum-olefin complexes, platinum-alcohol complexes, platinum-alcoholate complexes, platinum-ether complexes, platinum-aldehyde complexes, platinum-ketone complexes, including products of the reaction of $H_2PtCl_6\cdot 6H_2O$ and cyclohexanone, platinum-vinylsiloxane complexes, such as platinum-1,3-divinyl-1,1,3,3-tetramethyldisiloxane complexes, containing or not containing detectable inorganically bound halogen, bis(gamma-picoline)platinum dichloride, trimethylenedipyridine platinum dichloride, dicyclopentadiene platinum dichloride, (dimethyl sulfoxide)ethyleneplatinum(II) dichloride, and products of the reaction of platinum tetrachloride with an olefin and a primary amine or a secondary amine or a primary amine and a secondary amine, as disclosed in U.S. Pat. No. 4,292,434, such as the product of the reaction of platinum tetrachloride dissolved in 1-octene with sec.-butylamine, or ammoniumplatinum complexes as in EP-B 110,370.

The catalyst (3) is preferably employed in amounts of from 0.5 to 200 ppm by weight (parts by weight per million parts by weight), preferably in amounts of from 1 to 50 ppm by weight, calculated as elemental platinum and based on the total weight of the organic compound (1) and the organosilicon compound (2).

The process of this invention is preferably carried out under the pressure of the ambient atmosphere, i.e., at about 1020 hPa (abs.), but may also be carried out at elevated or reduced pressures.

The process of this invention is furthermore preferably carried out at a temperature of from 80° C. to 150° C., more preferably from 100° C. to 150° C., more preferably from 120° C. to 130° C.

In the process of this invention, inert, organic solvents may also be used, although the additional use of inert, organic solvents is not preferred. Examples of inert, organic solvents are toluene, xylene, octane isomers and butyl acetate.

Excess organic compound (1) and any inert organic solvent also used are preferably removed by distillation from the organosilicon compounds containing alkenyl groups prepared by the process of this invention.

The addition reaction of the organosilicon compound (2) containing at least one Si-bonded hydrogen atom per molecule with the organic compound (1) takes place, both for $x=0$ and $y=1$ and $x=1$ and $y=0$, selectively at the terminal triple bond and not at the terminal double bond, and for $x=1$ and $y=1$ selectively at the internal triple bond and not at the terminal double bonds. Thus, organopolysiloxanes containing alkenyl groups can be prepared directly from organopolysiloxane containing Si-bonded hydrogen atoms and an organic compound (1) without crosslinking occurring via the terminal double bonds. In addition, organosilicon compounds containing alkenyl groups are obtained according to the invention without double bond isomerization of the terminal double bond(s) from the end position into the chain.

The organopolysiloxanes (4), with which the organopolysiloxane containing alkenyl groups which is present after completion of the 1st step is optionally equilibrated, are preferably those selected from the group comprising linear organpolysiloxanes containing terminal triorganosiloxy groups, of the formula $R_3SiO(SiR_2O)_rSiR_3$, in which R is as defined above, and r is 0 or an integer having a value of from 1 to 1500, linear organopolysiloxanes containing terminal hydroxyl groups, of the formula $HO(SiR_2O)_sH$, in which R is as defined above, and s is an integer having a value of from 1 to 1500, cyclic organopolysiloxanes of the formula $(R_2SiO)_t$, in which R is as defined above, and t is an integer from 3 to 12, and copolymers comprising units of the formula $R_2SiO$ and $RSiO_{3/2}$.

in which R is as defined above.

The mixing ratios of the organopolysiloxanes employed in the second step of the process of the invention are determined merely through the desired proportion of alkenyl groups in the organopolysiloxanes produced in the optional 2nd step of the process of this invention and through the mean chain length desired.

In the equilibration carried out in the 2nd step of the process of this invention, basic catalysts which promote the equilibration are preferably employed. Examples of such catalysts are alkali metal hydroxides, such as sodium hydroxide and potassium hydroxide, trimethylbenzylammonium hydroxide and tetramethylammonium hydroxide. Alkali metal hydroxides are preferred.

Alkali metal hydroxides are preferably used in amounts of from 50 to 10,000 ppm (parts per million) by weight, in particular 500 to 2,000 ppm by weight, in each case based on the total weight of the organosilicon compounds employed. Although the use of acidic equilibration catalysts is possible, it is not preferred.

The optional equilibration carried out in the second step of the process of this invention is preferably carried out at from 80° C. to 150° C. and at a pressure of the ambient atmosphere, i.e., at about 1020 hPa (abs.). If desired, however, higher or lower pressures can also be used. The equilibration is preferably carried out in from 5 to 20 percent by weight, based on the total weight of the organosilicon compounds employed in each case, in water-immiscible solvents, such as toluene. Before work-up of the mixture obtained on equilibration, the catalyst can be deactivated.

The various steps of the process of this invention can be carried out successively in one reaction vessel or in separate reaction vessels. The steps are preferably carried out successively in a single reaction vessel. The process of this invention can be carried out batchwise, semicontinuously or fully continuously.

The organopolysiloxanes of this invention containing alkenyl groups can be crosslinked, like the organopolysiloxanes containing Si-bonded vinyl groups, using organopolysiloxanes containing Si-bonded hydrogen in the presence of hydrosilylation catalysts.

The organopolysiloxanes of this invention are used in compositions which contain (A) an organopolysiloxane of the formula (I), preferably of the formula (III), which contains alkenyl groups; (B) an organopolysiloxane which contains Si-bonded hydrogen atoms; and (C) a catalyst which promotes the addition reaction of Si-bonded hydrogen with an aliphatic multiple bond.

Component (B) is preferably an organopolysiloxane of the formula (IV), more preferably of the formula (VI).

Component (C) is preferably one of the abovementioned catalysts (3).

In addition, the compositions may contain further additives, such as (D) agents which retard the addition reaction of Si-bonded hydrogen with an aliphatic multiple bond at room temperature. Such inhibitors are described, for example, in U.S. Pat. No. 3,933,880. Examples of those inhibitors include acetylenically unsaturated alcohols, such as 3-methyl-1-butyn-3-ol, 1-ethynylcyclohexan-1-ol, 3,5-dimethyl-1-hexyn-3-ol, 3-methyl-1-pentyn-3-ol and the like.

The compositions containing the organopolysiloxanes of this invention are used for the preparation of adhesive-repellant release coatings.

PREPARATION OF 1,4-BIS(ALLYLOXY)-2-BUTYNE

About 600 g of sodium hydroxide were dissolved in 600 g of water. About 28 g of trimethylbenzylammonium chloride (0.1 mol), 220 g of 2-butyne-1,4-diol (2.5 mol) and 470 g of allyl chloride (6.0 mol) were added to the sodium hydroxide solution, and the mixture was refluxed with stirring for 8 hours. Water was added to the cooled reaction mixture to dissolve the precipitated sodium chloride to form a clear solution. The mixture was separated. The upper, organic phase was separated and washed with 200 ml of water. Any remaining water was removed from the organic phase by azeotropic distillation, and the organic phase was then subjected to fractional distillation under vacuum. About 381 g of 1,4-bis(allyloxy)-2-butyne (92 percent theory) were obtained at 71° C. to 72° C. and 6 hPa (abs.). The following data was obtained from the $^1$H-NMR spectrum, from which no impurities are detectable.

$^1$H-NMR spectrum:
(CDCl$_3$)

$\delta$ = 3.96 ppm (ddd , 4 H, —O—C$\underline{H}_2$—CH=)
4.10 ppm (s , 4 H, —O—C$\underline{H}_2$—C≡
5.11 ppm (ddtr, 2 H, —O—CH$_2$—CH=CH—H)
5.22 ppm (ddtr, 2 H, —O—CH$_2$—CH=C$\underline{H}$—H)
5.79 ppm (ddtr, 2 H, —O—CH$_2$—C$\underline{H}$=CH$_2$)

PREPARATION OF 2,5-BIS(ALLYLOXY)-3-HEXYNE

About 600 g of sodium hydroxide were dissolved in 600 g of water. About 28 g of trimethylbenzylammonium chloride (0.1 mol), 285 g of 3-hexyne-2,5-diol (2.5 mol) and 470 g of allyl chloride (6.0 mol) were added to the sodium hydroxide solution, and the mixture was refluxed with stirring for 8 hours. A sufficient amount of water was added to the cooled reaction mixture to dissolve the precipitated sodium chloride to form a clear solution. The mixture was permitted to stand until good phase separation occurred. The upper, organic phase was separated from the aqueous phase and washed with 200 ml of water. Any water remaining in the organic phase was removed from the organic phase by azeotropic distillation. The organic phase was then subjected to fractional distillation under vacuum. About 427 g of 2,5-bis(allyloxy)-3-hexyne (88 percent theory) were obtained as a colorless distillate at 62° C. to 63° C. and 6 hPa (abs.).

PREPARATION OF 2-ALLYLOXY-3-BUTYNE

About 600 g of sodium hydroxide were dissolved in 600 g of water. About 28 g of trimethylbenzylammonium chloride (0.1 mol), 350 g of 3-butyn-2-ol and 470 g of allyl chloride (6.0 mol) were added to the sodium hydroxide solution, and the mixture was refluxed with stirring for 8 hours. 1 liter of water was added to the cooled reaction mixture, forming two liquid phases which separated well. The upper, organic phase was separated off, washed twice with 200 ml of water in each case and distilled at atmospheric pressure over a short packed column. About 452 g of 2-allyloxy-3-butyne (82 percent of theory) were obtained at 109° C. to 111° C.

EXAMPLE 1

About 82 g of triethoxysilane were added dropwise at 125° C. to a solution of 1.4 mg of platinum, in the form of a solution of platinum tetrachloride in 1-octene, in 91 g of 1,4-bis(allyloxy)-2-butyne, prepared as described above. After a reaction time of 20 hours, determination of the hydrogen number under alkaline conditions indicated a conversion of 99.5 percent of the Si-bonded hydrogen in the triethoxysilane. About 128 g of a silane of the formula

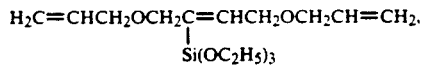

were obtained by distillation at 115° C. to 120° C. and 3 hPa (abs.). The silane obtained had an iodine number (the number which indicates how many g of iodine are bound per 100 g of substance) of 226 (theoretically: 231). The $^1$H-NMR spectrum provided the following data:

$^1$H-NMR Spectrum:
(CDCl$_3$)

$\delta$ = 1.21 ppm (tr , 9 H, Si—O—CH$_2$—C$\underline{H}_3$)
3.79 ppm (qu , 6 H, Si—O—C$\underline{H}_2$—CH$_3$)
3.93 ppm (ddd , 4 H, —OC$\underline{H}_2$—CH=CH$_2$)
4.03 ppm ("d", 2 H, —O—C$\underline{H}_2$—C=CH—CH$_2$—)
                                        |
                                        Si
4.12 ppm (d , 2 H, —O—CH$_2$—CH=C—C$\underline{H}_2$—)
                                        |
                                        Si
5.11 ppm (ddtr, 2 H, —O—CH$_2$—CH=CH—H)
5.22 ppm (ddtr, 2 H, —O—CH$_2$—CH=C$\underline{H}$—H)
5.84 ppm (ddtr, 2 H, —O—CH$_2$—C$\underline{H}$=CH$_2$)
6.31 ppm (trtr , 1 H, —O—CH$_2$—C$\underline{H}$=C—CH$_2$)
                                        |
                                        Si

EXAMPLE 2

About 1.4 mg of platinum, in the form of platinum tetrachloride dissolved in 1-octene, were dissolved in 96.3 g of 1,4-bis(allyloxy)-2-butyne prepared as described above. The solution was warmed under nitrogen to 125° C. About 227 g of an α,w-dihydrogendimethylpolysiloxane containing 0.22 percent by weight of Si-bonded hydrogen were then added dropwise to the warmed solution. After the mixture was stirred for about 8 hours at 125° C., more than 97 percent of the Si-bonded hydrogen in the α,w-dihydrogendimethylpolysiloxane had been converted. Excess 1,4-bis(allyloxy)-2-butyne was removed from the crude product by distillation at 140° C. and $10^{-3}$ hPa (abs.). About 250 g (81 percent theory) of a yellowish oil having a viscosity of 24 mm$^2 \cdot$s$^{-1}$ at 25° C. were obtained. According to the $^1$H-NMR spectrum, the dimethylpolysiloxane obtained in this way contained one Si-bonded radical of the formula H$_2$C=CHCH$_2$OCH$_2$C=CHCH$_2$OCH$_2$CH=CH$_2$.
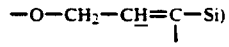

in each of the terminal units and had a mean chain length of 16. The $^1$H-NMR spectrum also indicated a value of about 0.02 for the (Si—CH$_2$—CH$_2$—) group: (Si—C=CH—) group ratio, which means that the ratio between addition at the allyl group to addition at the butyne group in 1,4-bis(allyloxy)-2-butyne was about 1:100. The $^1$H-NMR spectrum also gives the following data:

$^1$H-NMR spectrum δ=6.06 ppm (tr, 1 H,

—O—CH$_2$—C$\underline{H}$=C—Si)
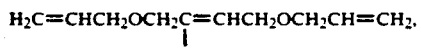

(CDCl$_3$)

EXAMPLE 3

About 1.4 mg of platinum, in the form of platinum tetrachloride dissolved in 1-octene, were dissolved in 116 g of 2,5-bis(allyloxy)-3-hexyne prepared as described above. The solution was warmed under nitrogen to 130° C. About 227 g of an α,w-dihydrogendimethylpolysiloxane containing 0.22 percent by weight of Si-bonded hydrogen were then added dropwise to the warmed solution. After the mixture was stirred for about 8 hours at 125° C., 95 percent of the Si-bonded hydrogen in the α,w-dihydrogendimethylpolysiloxane were converted. Excess 2,5-bis(allyloxy)-3-hexyne was removed from the crude product by distillation at 140° C. and $10^{-3}$ hPa (abs.). About 227 g (73 percent theory) of an oil having a viscosity of 46 mm$^2 \cdot$s$^{-1}$ at 25° C. were obtained. According to the $^1$H-NMR spectrum, the dimethylpolysiloxane obtained in this way contained one Si-bonded radical of the formula

H$_2$C=CHCH$_2$OCH(CH$_3$)C=CHCH(CH$_3$)OCH$_2$CH=CH$_2$.
| in each of the terminal units and had a mean chain length of 20. The $^1$H-NMR spectrum also indicated a value of about 0.04 for the (Si—CH$_2$—CH$_2$—) group:

(Si—C=CH—)
| group ratio, which means that the ratio between addition at the allyl group and addition at the hexyne group in 2,5-bis(allyloxy)-3-hexyne was about 1:50. The $^1$H-NMR spectrum also gave the following data:

$^1$H-NMR spectrum: δ=5.80 ppm (dd, 1 H,

—O—CH—C$\underline{H}$=C—Si)
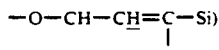

(CDCl$_3$)

EXAMPLE 4

About 2.7 mg of platinum, in the form of platinum tetrachloride dissolved in 1-octene, were dissolved in 96.3 g of 1,4-bis(allyloxy)-2-butyne. The solution was warmed under nitrogen to 125° C. About 91 g of a copolymer comprising methylhydrogensiloxane, dimethylsiloxane and trimethylsiloxane units and having a viscosity of 11.2 mm$^2 \cdot$s$^{-1}$ at 25° C. and containing 0.55 percent by weight of Si-bonded hydrogen were slowly added dropwise to this solution at 125° C. After the mixture was stirred for about 6 hours at 125° C., 98 percent of the Si-bonded hydrogen in the copolymer was converted. The crude product was filtered, and the volatile constituents were removed from the crude product by distillation at 140° C. and $10^{-3}$ hPa (abs.). About 110 g (71 percent of theory) of a clear, yellowish oil having a viscosity of 150 mm$^2 \cdot$s$^{-1}$ at 25° C. were obtained. The $^1$H-NMR spectrum indicated a value of about 0.025 for the (Si—CH$_2$—CH$_2$) group:

(Si—C=CH—)
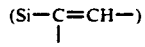

group ratio, which means that the ratio between addition of the (CH$_3$)HSiO group at the allyl group and addition of the (CH3)HSiO group at the butyne group in 1,4-bis(allyloxy)2-butyne was about 1:80. The following data were obtained from the $^1$H-NMR spectrum and the $^{29}$Si-NMR spectrum:

$^1$H-NMR spectrum:
(CDCl$_3$)

δ = 6.2 ppm (1 H, —O—CH—C$\underline{H}$=C—Si)

$^{29}$Si-NMR-spectrum:
(C$_6$D$_6$)

δ = +7.9 ppm ⎤
            ├─ (2 Si, (CH$_3$)$_3$SiO$_\frac{1}{2}$)
    +7.3 ppm ⎦
  −20.7 ppm (10.5 Si, (CH$_3$)$_2$SiO)
  −35.8 ppm (6 Si, —CH=C—Si(CH$_3$)O)
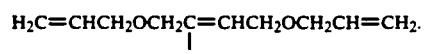

The spectra indicated a mean molecular weight of about 2,300. Each molecule contained an average of six Si-bonded radicals of the formula H$_2$C=CHCH$_2$OCH$_2$C=CHCH$_2$OCH$_2$CH=CH$_2$.
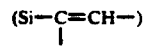

EXAMPLE 5

About 5 mg of a solution of platinum tetrachloride in 1-octene, each ml of solution containing 40 mg of platinum. were added to 20.0 g of 2-allyloxy-3-butyne prepared as described above. The solution was warmed to 115° C. under a nitrogen atmosphere. About 319.1 g of an α,w-dihydrogendimethylpolysiloxane containing 0.047 percent by weight of Si-bonded hydrogen were then added dropwise to the warmed solution. After a reaction time of about 6 hours at 115° C., more than 99 percent of the Si-bonded hydrogen in the α,w-dihydrogendimethylpolysiloxane were converted. The volatile constituents, such as excess 2-allyloxy-3-butyne, were removed from the crude product by distillation at 100° C. and 12 hPa (abs.). About 315 g of a yellowish oil which had a viscosity of 92 mm$^2 \cdot$s$^{-1}$ at 25° C. and an iodine number (the number which indicates how many g of iodine are bound by 100 g of 21.3 were obtained. According to the $^1$H-NMR spectrum, the dimethylpolysiloxane obtained in this way contains terminal Si-bonded radicals of the formulas

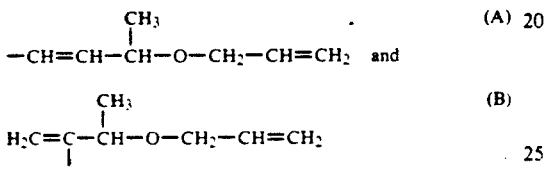

the terminal radicals being a mixture of isomers having a ratio of 65:35.

Bonds of the type Si—CH$_2$—CH$_2$—, which would originate from the addition of the Si-H bonds at the allyl group in the 2-allyloxy-3-butyne, cannot be detected in the $^1$H-NMR spectrum. The following data was obtained from the $^1$H-NMR spectrum:

$^1$H-NMR spectrum: δ = 1.23 ppm [d, 3H. C$\underline{H}_3$—CH—O;
(CDCl$_3$)          isomer (A)]
             = 1.27 ppm [d, 3H. C$\underline{H}_3$—CH—O;
              isomer (B)].

EXAMPLE 6

About 31 g of the product from Example 2 were stirred for 16 hours at 140° C. under a nitrogen atmosphere with 208 g of cyclodecamethylpentasiloxane and 250 mg of KOH in 300 mg of methanol. About 0.5 g of glacial acetic acid was added while the reaction mixture cooled, and the cooled reaction mixture was then filtered. The volatile constituents were removed from the crude product by distillation at 100° C. and 5 hPa. About 216 g of a dimethylpolysiloxane which, according to the $^1$H-NMR spectrum, contained one Si-bonded radical of the formula

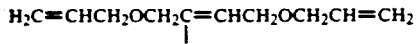

in each of the terminal units and had a viscosity of 460 mm$^2 \cdot$s$^{-1}$ at 25° C. were obtained.

The iodine number of 12.0, determined for the dimethylpolysiloxane obtained in this way, indicated an H$_2$C=CH equivalent weight of 3175 g per terminal carbon-carbon double bond.

EXAMPLE 7

About 20 g of the product from Example 6 were mixed with 1.0 g of a copolymer comprising trimethylsiloxane units and methylhydrogensiloxane units, having a viscosity of about 30 mm$^2 \cdot$s$^{-1}$ at 25° C., 50 g of 2-methyl-3-butyn-2-ol and 2 mg of platinum, in the form of platinum tetrachloride dissolved in 1-octene. The mixture was coated onto paper in a thickness of 2–3 μm. It cured at 120° C. in 12 seconds to form a tackfree coating. Gelation of the mixture was complete after 21 hours at 25° C.

What is claimed is:

1. An organosilicon compound containing alkenyl groups comprising units of the average formula

wherein R is an identical or different monovalent, hydrocarbon radical having from 1 to 18 carbon atom(s) or a monovalent halogenated hydrocarbon radical having from 1 to 18 carbon atom(s) per radical, R$^1$ are identical or different alkyl radicals having 1 to 8 carbon atom(s) or an alkyl radical containing 1 to 8 carbon atoms containing an ether oxygen atom, and A is a radical of the formula

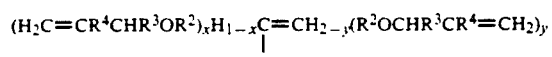

in which R$^2$ is an alkylene radical having 1 to 4 carbon atom(s); R$^3$ is a hydrogen atom or a methyl radical,; R$^4$ is a hydrogen atom, a methyl or ethyl radical; x is 0 or 1, y is 0 or 1, with the proviso that the sum x+y is 1 or 2; a is 0 or 1, with an average value of 0.003 to 1.0; b is 0, 1, 2 or 3, with an average value of 0.0 to 3.0; c is 0, 1, 2 or 3, with an average value of 0.0 to 3.0; and the sum a+b+c≦4, with an average value of from 1.5 to 4, with the proviso that each molecule contains at least one radical A.

2. An organosilicon compound containing alkenyl groups of claim 1, comprising a silane or an organopolysiloxane.

3. An organosilicon compound containing alkenyl groups of claim 1 or 2, comprising a silane of the formula

in which R is an independently selected monovalent, hydrocarbon radical having from 1 to about 18 carbon atoms or a monovalent halogenated hydrocarbon radical having from 1 to about 18 carbon atom(s) per radical, R$^1$ is an independently selected alkyl radical having 1 to 8 carbon atoms or alkyl radicals substituted with an ether oxygen having 1 to 8 carbon atom(s), and A is a radical of the formula

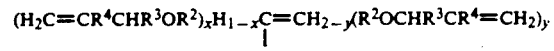

in which R$^2$ is an independently selected alkylene radical having 1 to 4 carbon atom(s); R$^3$ is an independently selected hydrogen atom or a methyl radical; R$^4$ is an independently selected hydrogen atom, methyl or ethyl radical; x is 0 or 1, y is 0 or 1, with the proviso that the sum x+y is 1 or 2; and d is 0, 1 or 2.

4. An organosilicon compound containing alkenyl groups of claim 1 or 2, comprising an organopolysiloxane of the formula $$A_gR_{3-g}SiO(SiR_2O)_n(SiRAO)_mSiR_{3-g}A_g \quad (III)$$

in which R is an independently selected monovalent, hydrocarbon radical having from 1 to 18 carbon atoms or a monovalent halogenated hydrocarbon radical having from 1 to 18 carbon atom(s), and A is a radical of the formula $$(H_2C=CR^4CHR^3OR^2)_xH_{1-x}C=CH_{2-y}(R^2OCHR^3CR^4=CH_2)_y$$

in which $R^2$ is an independently selected alkylene radical having 1 to 4 carbon atom(s); $R^3$ is an independently selected hydrogen atom or methyl radical; $R^4$ is an independently selected hydrogen atom, methyl or ethyl radical; x is 0 or 1, y is 0 or 1, with the proviso that the sum x+y is 1 or 2; g is 0 or 1; n is 0 or an integer from 1 to 1,500; and m is 0 or an integer from 1 to 100, with the proviso that each molecule contains at least one A radical.

5. An organosilicon compound containing alkenyl groups of claim 1 or 2, wherein x and y are each 1.

6. An organosilicon compound containing alkenyl groups of claim 1 or 2, wherein A is a radical of the formula $$H_2C=CHCH_2OCH_2C=CHCH_2OCH_2CH=CH_2.$$

7. A process for the preparation of an organosilicon compound containing alkenyl groups of claim 1, which comprises reacting an organic compound of the formula $$(H_2C=CR^4CHR^3OR^2)_xH_{1-x}C=CH_1-_y(R^2OCHR^3CR^4=CH_2)_y \quad (1)$$

in which $R^2$ is an independently selected alkylene radical having 1 to 4 carbon atom(s); $R^3$ is independently selected from a hydrogen atom or a methyl radical; $R^4$ is independently selected from a hydrogen atom, methyl or ethyl radical; x is 0 or 1, and y is 0 or 1, with the proviso that the sum x+y is 1 or 2; with an organosilicon compound (2) containing at least one Si-bonded hydrogen atom in its molecule, in the presence of a catalyst (3) which promotes the addition reaction of Si-bonded hydrogen with an aliphatic multiple bond.

8. The process of claim 7, wherein the organosilicon compound (2) containing at least one Si-bonded hydrogen atom in its molecule is a silane of the formula $$HR_dSi(OR^1)_{3-d} \quad (V),$$

wherein the R radicals are identical or different monovalent hydrocarbon radicals having from 1 to about 18 carbon atoms or monovalent halogenated hydrocarbon radicals having from 1 to 18 carbon atom(s). $R^1$ is an identical or different alkyl radical having from 1 to about 8 carbon atom(s) per radical, or a hydrocarbon radical having from 1 to about 8 carbon atoms containing ether oxygen; and d is 0, 1 or 2.

9. The process of claim 7, wherein the organosilicon compound (2) containing at least one Si-bonded hydrogen atom in its molecule is an organopolysiloxane of the formula $$H_hR_{3-h}SiO(SiR_2O)_o(SiRHO)_pSiR_{3-h}H_h \quad (VI).$$

in which the R radicals are identical or different monovalent hydrocarbon radicals containing from 1 to 18 carbon atoms, or monovalent halogenated hydrocarbon radicals having from 1 to 18 carbon atom(s); the $R^1$ radicals are identical or different alkyl radicals having 1 to 8 carbon atom(S) per radical, or hydrocarbon radicals having from 1 to 8 carbon atoms containing ether oxygen; h is 0 or 1; o is 0 or an integer from 1 to 1,500; and p is 0 or an integer from 1 to 100.

10. A composition containing (A) an organopolysiloxane containing alkenyl groups as claimed in claim 1 or 2; (B) an organopolysiloxane containing Si-bonded hydrogen atoms; and (C) a catalyst which promotes the addition reaction of Si-bonded hydrogen with an aliphatic multiple bond.

11. A process for the preparation of an organosilicon compound containing alkenyl groups, which comprises reacting an organic compound of the formula $$(H_2C=CR^4CHR^3OR^2)_xH_{1-x}C=CH_1-_y(R^2OCHR^3CR^4=CH_2)_y \quad (1)$$

in which $R^2$ is an independently selected alkylene radical having 1 to 4 carbon atom(s); $R^3$ is independently selected from a hydrogen atom or a methyl radical; $R^4$ is independently selected from a hydrogen atom, methyl or ethyl radical; x is 0 or 1, and y is 0 or 1, with the proviso that the sum x+y is 1 or 2; with an organosilicon compound (2) containing at least one Si-bonded hydrogen atom in its molecule, in the presence of a catalyst (3) which promotes the addition reaction of Si-bonded hydrogen with an aliphatic multiple bond, and thereafter equilibrating the organopolysiloxane composition containing alkenyl groups with an organopolysiloxane (4) selected from the group consisting of linear organopolysiloxanes containing terminal triorganosiloxy groups, linear organopolysiloanes containing terminal hydroxyl groups, cyclic organopolysiloxanes and copolymers containing diorganopolysiloxane and monoorganosiloxane units.

* * * * *